(12) United States Patent
Itoyama et al.

(10) Patent No.: US 6,743,261 B2
(45) Date of Patent: Jun. 1, 2004

(54) FUNCTIONALIZED FIBER MATERIAL AND METHOD FOR TREATING FIBER MATERIAL THEREFOR

(75) Inventors: Koki Itoyama, Shizuoka-ken (JP); Takatoshi Fujii, Shizuoka-ken (JP)

(73) Assignee: Fuji Spinning Co., Ltd., Tokyo (JP)

( * ) Notice: Subject to any disclaimer, the term of this patent is extended or adjusted under 35 U.S.C. 154(b) by 265 days.

(21) Appl. No.: 09/919,928

(22) Filed: Aug. 2, 2001

(65) Prior Publication Data

US 2002/0038479 A1 Apr. 4, 2002

(30) Foreign Application Priority Data

Aug. 11, 2000 (JP) .......................................... 2000-244068

(51) Int. Cl.⁷ ........................................... D06M 13/224
(52) U.S. Cl. ........................ 8/115.6; 8/115.56; 442/121; 442/123
(58) Field of Search ................................ 442/121, 123; 8/115.6, 115.56; 427/389.9

(56) References Cited

U.S. PATENT DOCUMENTS 5,232,769 A * 8/1993 Yamoto et al.

FOREIGN PATENT DOCUMENTS

| JP | 3-13355 | 2/1991 |
|----|---------|--------|
| JP | 5-32537 | 2/1993 |
| JP | 10-131042 | 5/1998 |
| JP | 10-331070 | 12/1998 |

\* cited by examiner

Primary Examiner—Margaret Einsmann
(74) Attorney, Agent, or Firm—Birch, Stewart, Kolasch & Birch, LLP

(57) ABSTRACT

The present invention discloses a functionalized fiber material treated with a emulsion containing an ascorbic acid derivative which is hardly soluble in water, wherein the ascorbic acid derivative which is hardly soluble in water is preferably tetraalkylester of L-ascorbic acid. Said treatment method comprises treating a fiber material with an emulsion comprising a mixture of an ascorbic acid derivative which is hardly soluble in water, an anionic surfactant or a combination of an anionic surfactant and a nonionic surfactant, and water, wherein a concentration of the ascorbic acid derivative which is hardly soluble in water is 0.05 to 10 % by weight. The functionalized fiber material of the present invention enables a sustained discharge of the active ingredient without losing the moisture absorption and release properties possessed by the fiber.

11 Claims, No Drawings

FUNCTIONALIZED FIBER MATERIAL AND METHOD FOR TREATING FIBER MATERIAL THEREFOR

BACKGROUND OF THE INVENTION

1. Field of the Invention

The present invention relates to a functionalized fiber material which has a sustained discharge function for an agent creating a skin care effect with a resistance for washing without losing the feeling and the hygroscopic property essentially possessed by the fiber material itself, and a method for treating a fiber material to obtain it, wherein said functionalized fiber material can be suitably utilized in a fabricing field such as underwears and shirts.

2. Description of Related Art

Ascorbic acid is a natural antioxidant agent and widely used in cosmetics and foods for health for the purposes of skin care and preventing oxidation of foods. Applications of ascorbic acid to fiber products have been tried since before in order to obtain a function of skin care or deodorization. However, as ascorbic acid is oxidized very easily, it loses its antioxidant property within a short time even if it is simply added on a fiber, and is also poor in a resistance for washing if it is only simply added thereon. Accordingly, in the application of ascorbic acid to fibers, it has been important points to stabilize ascorbic acid and improve its resistance to washing when it is added on fibers.

For example, JP-B-3-13355 discloses a method for a deodorization treatment having a resistance for washing wherein ascorbic acid and various ferrous salts are fixed to a fiber using a synthetic resin. However, the method for fixing ascorbic acid to a fiber using a synthetic resin has weak points such as deterioration of a feeling of the fiber and spoiling a hygroscopic property essential to the fiber when natural fibers and cellulose fibers are treated. Further, as the methods intending to solve the instability of ascorbic acid, JP-A-10-131042 discloses a softening finishing agent which has small capsules encapsulating an antioxidant comprising an alkyl ester of ascorbic acid in order to add a deodorizing function, and JP-A-10-331070 discloses an antioxidant fiber material, wherein an antioxidant is stabilized by forming a complex between the antioxidant and a protein, and a fiber product is treated with said complex.

A fiber finishing composition disclosed in JP-A-10-131042 has a superior stability because an ascorbic acid derivative is used, but is poor in a durability because the composition of said invention has been designed as a softening finishing agent to be used after washing without taking account of a resistance to washing at all. Furthermore, an antioxidant fiber material described in JP-A-10-331070 is the one intended for an application field of a food packaging materials, and has no function of sustained discharge because it has been treated together with a cross-linking agent to improve a durability, although it has a stabilized antioxidant and an acceptable resistance to washing.

On the other hand, JP-A-5-32537 discloses derivatives of a compound such as ascorbic acid, phosphoric ester of ascorbic acid and sulfuric ester of ascorbic acid, used for a skin care cosmetics as a substance having an action to promote a collagen synthesis, but this cosmetic does not have a function of sustained discharge of ascorbic acid to skin.

SUMMARY OF THE INVENTION

An object of the present invention is to provide a functionalized fiber material having a skin care effect without losing the feeling and the hygroscopic property which are essentially possessed by the fiber.

Another object of the present invention is to provide a fiber material which allows a sustained discharge of an ascorbic acid derivative stuck on the fiber product by an action of a fat component such as sebum present on a skin surface of the human body.

Further object of the present invention is to provide a fiber material on which an ascorbic acid derivative having a resistance to washing sticks.

Still further object of the present invention is to provide a method for treating a fiber material to obtain said fuctionalized fiber material.

The present invention consists of a functionalized fiber material treated with an emulsion containing an ascorbic acid derivative which is hardly soluble in water, and said ascorbic acid derivative which is hardly soluble in water is preferably a polyalkylester of L-ascorbic acid. The treatment method comprises addition of an emulsion containing an ascorbic acid derivative which is hardly soluble in water on the fiber material, wherein said emulsion comprises a mixture of an ascorbic acid derivative which is hardly soluble in water, an anionic surfactant optionally together with a nonionic surfactant and water, and the concentration of the ascorbic acid derivative which is hardly soluble in water in said emulsion is from 0.05 to 10% by weight.

DETAILED DESCRIPTION OF THE INVENTION

The fiber materials used in the present invention are not specially limited. The fiber materials may be natural fibers such as cotton, wool, silk and etc., regenerated fibers such as rayon, polynosic, cellulose acetate and etc., synthetic fibers such as polyester, nylon, acrylic and etc. or combined filaments made of one or more kinds thereof, which are usually used as fabricing and knitting. Further, in the case of the regenerated fiber or the synthetic fiber, it may include a fiber material containing a substance to express other functions. Said substance contained in the fiber material is not specially limited so long as it does not disturb the sustained discharge function of the ascorbic acid derivative.

In the case of the rayon or the polynosic, the fiber material may include a modified regenerated cellulose fiber having an improved resistance to swelling with water, which is obtained by adding and mixing a cross-linking agent into a cellulose viscose solution then spinning said solution, or a modified regenerated cellulose fiber having an improved resistance to swelling with water and fibrillation character, which is obtained by adding and mixing a cross-linking agent into a cellulose viscose solution then spinning said solution followed by contacting with an aqueous solution of a cross-linking agent.

In the above case, in order to express other function such as antibacterial action, deodorization action and an improved dyeability, a functionalizing agent such as fine granular chitosan, fine balloon particles, anionizing agent can, of course, be used together with the cross-linking agent. Form of the fiber material may be any of raw fiber, spun yarn, knitted or woven fabric, and fiber product. Furthermore, the fiber material with each of the above forms may have been treated in advance to give another function so long as the treatment does not inhibit the sustained discharge of the ascorbic acid derivative, but in this case, said treatment should be applied preferably before the treatment of the present invention, and particularly said treatment using a cross-linking agent must be applied before the treatment of the present invention. In the case when the fiber material is raw fiber, spun yarn, or knitted or woven fabric, they are used as a sewing fiber material for fabricing.

The ascorbic acid derivative which is hardly soluble in water to be used in the present invention is not specially limited so long as the derivatives which are soluble in an organic solvent, and includes, for example, monoalkylesters of L-ascorbic acid, dialkylesters of L-ascorbic acid, trialkylesters of L-ascorbic acid, tetraalkylesters of L-ascorbic acid and the like. Among them, tetraalkylesters of L-ascorbic acid is preferable from the viewpoint of a resistance to washing and a stability. The tetraalkylesters of L-ascorbic acid includes a isopalmitoyl or a stearoyl derivative.

The surfactants to be used for emulsifying the above described ascorbic acid derivative are desirably an anionic surfactant. When an ascorbic acid derivative can not be sufficiently emulsified due to an lower emulsifying power by using an anionic surfactant alone, a nonionic surfactant can be used as in a combination with the anionic surfactant. The anionic surfactants to be used in the present invention are not specially limited, and includes, for example, a various kinds of fatty acid soaps, sodium lauryl sulfate, sodium higher alcohol sulfate, sodium dodecylbenzenesulfonate, sodium dialkylphosphosuccinate, potassium alkylphosphate, sodium polyoxyethylenealkylether sulfate, and the like. Further, the nonionic surfactants which can be used in the present invention include, for example, polyoxyethylene derivatives, sorbitan monoalkylates, sorbitan dialkylates, sorbitan trialkylates and the like. The nonionic surfactant can be suitably selected from the above group.

The method for treating a fiber material of the present invention comprises, firstly obtaining an emulsion containing an ascorbic acid derivative which is hardly soluble in water by mixing, stirring and emulsifying the ascorbic acid derivative and water, dipping a fiber material therein, squeezing the fiber material at the squeezing rate from 60 to 120%, subsequently drying at the temperature from 80 to 200° C. for the time from 1 to 30 minutes. The mean for adding the emulsion containing an ascorbic acid derivative on the fiber material may be coating or spraying the emulsion as well as dipping therein to stick on the fiber material.

A fabric can be made of a modified regenerated cellulose fiber with an improved swelling property to water, which is obtained by adding and mixing a cross-linking agent to a cellulose viscose solution then spinning said solution, subsequently said fabric can be treated with a cross-linking agent in order to jointly improve a fibrillation character. In such a treatment, if said treatment with a cross-linking agent is conducted after the treatment with an emulsion of the ascorbic acid derivative of the present invention, the cross-linking agent reacts with the ascorbic acid derivative and a regenerated cellulose fiber, resulting in reducing the sustained discharge function of an ascorbic acid derivative by an action of a sebum and the like. Accordingly, said treatment with a cross-linking agent must be conducted before the treatment with an emulsion of the ascorbic acid derivative of the present invention.

Concerning to the concentration of the emulsion to be used for treating a fiber material, the concentration of the ascorbic acid derivative in the emulsion is preferably in the range from 0.05 to 10% by weight. The concentration lower than 0.05% by weight can not exhibit an expected skin care effect, and the concentration over 10% by weight unsuitably increase a viscosity of the emulsion and make it difficult to treat a fiber material evenly. The concentration of the surfactant in this process is not specially limited so long as it enables to emulsify. However, the concentration is preferably as low as possible within a range enabling to emulsify, because too much surfactant to an amount of an ascorbic acid derivative deteriorates a resistance to washing. The method for stirring to obtain the emulsion is not specially limited, and, for example, stirring with a homogenizer may be used.

Furthermore, in emulsifying, though an ascorbic acid derivative can be emulsified only with a surfactant, an addition of an organic solvent can be employed in order to adjust a concentration and a viscosity of the emulsion. The organic solvent to be used is not specially limited so long as it can dissolve the ascorbic acid derivative, and includes, for example, oleic acid, squalane and derivatives thereof, hexane, diethylether, ethyl acetate, dodecanol, and the like.

As obvious from the examples described hereinunder, when tetraalkylesters of L-ascorbic acid as an ascorbic acid derivative which is hardly soluble in water is used for treating a fiber material by the treatment method of the present invention, the stuck amount of the tetraalkylesters of L-ascorbic acid on a fiber material before washing in the range from 0.30 to 48.0 mg/g gives a functionalized fiber material which is excellent in a sustained discharge function and moisture absorption and release properties.

The ascorbic acid derivative stuck on a fiber material according to the present invention shows an excellent resistance to washing in such an extent that 50% or more of the initial amount remains even after 10 times of washings. This is because a hydrophilic property of the derivative is very weak. When an ascorbic acid derivative is used in cosmetics, this derivative is usually incorporated into a skin layer and regenerate an ascorbic acid by an action of an enzyme to express the effect. The ascorbic acid derivatives stuck on a fiber material do not express an expected antioxidant property in a condition as stuck on a fiber, but once the fiber product is worn, the derivative is discharged slowly on a skin by an action of a fat such as sebum of the wearer and incorporated into a skin finally to express the effect.

According to the present invention, falling off of the ascorbic acid derivatives by washing can be suppressed, and in addition, it is presumed that a skin care effect can be expressed by discharging said derivatives gradually on a skin by an action of a fat component such as sebum present on a skin surface of the human body, and being incorporated into a skin layer since said derivatives are well dissolved in a fat such as sebum. Furthermore, The treatment of the present invention does not give any change in a feeling and moisture absorption release properties possessed by the fiber material.

EXAMPLES

Hereinunder, the present invention will be described concretely, but the present invention is not limited within the range of these examples. Measurements and evaluations in these examples were conducted according to the following methods.

Measurement of the Stuck Amounts of Ascorbic Acid Derivatives

A test fabric was dipped in isopropyl alcohol, followed by shaking at 37° C. for 2 hours, then the supernatant was analyzed by a HPLC (high performance liquid chromatography). An amount of the ascorbic acid derivative stuck on the fiber was calculated from an area of the peak of ascorbic acid derivative obtained.

Measurement of the Stuck Amount of Ascorbic Acid

A test fabric was dipped in an artificial sweat (JIS L0848-5. 1), followed by shaking at 37° C. for 2 hours, then the supernatant was analyzed by a HPLC (high performance liquid chromatography). An amount of ascorbic acid stuck on the fiber was calculated from an area of the peak of ascorbic acid obtained.

Evaluation of the Sustained Discharge Function

A test fabric was added with oleic acid so that the stuck amount became from 0.3 to 0.5% o.w.f, then washed. After 1, 4 and 10 times of washings, the ascorbic acid derivative remaining on the test fabric was determined according to the above described methods to measure a discharging condition of the ascorbic acid derivative by a fat. As for the samples treated with ascorbic acid, ascorbic acid instead of the ascorbic acid derivative was determined to measure a discharging condition of ascorbic acid by a fat.

Evaluation of the Feeling

Feeling of the test fabrics were judged by means of a handling test by 10 inspectors. Each inspector scored 1 point for a sample with a good feeling and 0 point for a sample with a bad feeling for each sample of the test fabrics. Feeling of the sample was judged according to the following criteria based on the total score of the sample.

① 8–10 points ◯(Superior)
② 4–7 points Δ(Good)
③ 0–3 points ×(Poor)

Evaluation of Moisture Absorption and Release

About 1 g of a sample was put into a weighting bottle which had a weight of $W_h$g, dried at 105° C. for 60 minutes with a cap being opened, cooled by leaving in a desiccator containing silica gel, then weighed as $W_0$ g. Subsequently, the sample in the bottle was kept in a desiccator which was kept at 60% RH overnight, then kept in a thermo-hygrostat being conditioned at 35° C. and 90% RH with a cap opened. After 60 minutes, the weighting bottle was taken out with a cap closed to be weighed as $W_2$ g. From these results, the moisture absorption and release were calculated according to the following formulae, respectively.

Formula 1

$$\text{Moisture absorption } (\%) = (W_1 - W_0)/(W_0 - W_h) \times 100$$

Formula 2

$$\text{Moisture release } (\%) = (W_1 - W_2)/(W_0 - W_h) \times 100$$

Example 1

Tetraisopalmitic acid ester of ascorbic acid as an ascorbic acid derivative (trade name: VC-IP, made by Nikko Chemicals Co., Ltd.), squalane, dodecanol, anionic surfactant (trade name: Levenol WX, made by Kao Corp.) and nonionic surfactant (trade name: Leodol, made by Kao Corp.) were mixed as shown in Table 1, respectively. Water was added to each mixture so that total amount of each mixture became 1 kg, followed by emulsifying using a homogenizer to obtain 6 kinds of emulsions of the ascorbic acid derivative, which were named as emulsions 1 to 6, respectively. The emulsion 6 had an increased viscosity due to a too high concentration as 15% of the ascorbic acid derivative, and failed to obtain an emulsion suitable for the present invention. Five pieces of fabrics made of cotton 100%, each having a size of 30 cm×30 cm, were dipped into each of the emulsions 1 to 5, respectively, followed by squeezing at the squeezing rate of 90%, and the heat treatment at 120° C. for 5 minutes, to obtain test fabrics of the samples 1 to 5, respectively. As a Comparative Example, a test fabric of the sample 6 was obtained similarly as in the samples 1 to 5 except for using 1 kg of an aqueous solution containing 1 g of ascorbic acid instead of the emulsions 1 to 5.

The obtained test fabrics of the samples 1 to 6 were washed 10 times with a detergent for general washing (trade name: Attack, made by Kao Corp.) using a conventional washing machine. The stuck amounts of ascorbic acid derivative and ascorbic acid of the samples 1 to 6 before and after 10 times of washings were measured. Independently from these tests, evaluations of sustained discharge functions, moisture absorption and discharge properties, and feelings of the samples 1 to 6 were carried out. The evaluations of the release functions were conducted by measuring the remaining amounts of the ascorbic acid derivative and ascorbic acid after 1 time, 4 times and 10 times of washings with additions of oleic acid to the samples 1 to 6, respectively. Results are shown in Table 2. In addition, evaluations of moisture absorption and release properties and feelings on the untreated fabric same to the one used in these tests were also carried out. Results are also shown in Table 2.

In Table 2, the samples 2 to 5, which were the test fabrics treated with the emulsions containing 0.05 to 10% of the ascorbic acid derivative, showed remaining of 50% or more of the ascorbic acid derivative even after 10 times of washings, proving a very high resistance to washing. Further, in the sustained discharge property test in which the remaining amounts of ascorbic acid derivative were examined, a sufficient level of the sustained discharge function could be confirmed. However, the test fabric of the sample 1 which was treated with the emulsion containing 0.03% of the ascorbic acid derivative showed a low level of the initial stuck amount, and the remaining amount so remarkably decreased that remaining amount could hardly be found after one time of the washing with the addition of oleic acid, proving not to be able to give an sufficient level of the sustained discharge function. On the other hand, the sample 6 as a Comparative Example treated with ascorbic acid showed a very low resistance to washing showing falling off of almost all of ascorbic acid by the washing. Furthermore, all of these samples did not show a decrease in the feeling and the moisture absorption and release properties differing from the untreated fabric.

TABLE 1

| Emulsion No. | VC-IP (g) | Squalane (g) | Dodecanol (g) | Nonionic surfactant (g) | Anionic surfactant (g) |
| --- | --- | --- | --- | --- | --- |
| Emulsion 1 | 0.3 | 1.5 | 0.3 | 0.2 | 0.2 |
| Emulsion 2 | 0.5 | 2.5 | 0.5 | 0.4 | 0.4 |
| Emulsion 3 | 1 | 5 | 1 | 0.8 | 0.8 |
| Emulsion 4 | 50 | — | 50 | 40 | 40 |
| Emulsion 5 | 100 | — | 100 | 80 | 80 |
| Emulsion 6 | 150 | — | 150 | 120 | 120 |

TABLE 2

| Sample No. | Stuck amount (mg/g) Before W* | Stuck amount (mg/g) After 10 W* | Sustained discharge function (mg/g) After 1 W* | Sustained discharge function (mg/g) After 4 W* | Sustained discharge function (mg/g) After 10 W* | Feeling | Moisture absorption & release (%) Absorption | Moisture absorption & release (%) Release |
|---|---|---|---|---|---|---|---|---|
| Sample 1 | 0.10 | 0 | 0 | 0 | 0 | ○ | 12.5 | 6.9 |
| Sample 2 | 0.30 | 0.13 | 0.15 | 0.05 | 0.02 | ○ | 12.5 | 6.9 |
| Sample 3 | 0.46 | 0.25 | 0.18 | 0.10 | 0.06 | ○ | 12.3 | 6.8 |
| Sample 4 | 20.3 | 10.2 | 8.9 | 3.0 | 1.5 | ○ | 12.2 | 6.5 |
| Sample 5 | 45.0 | 21.3 | 15.6 | 5.8 | 2.3 | ○ | 12.2 | 6.6 |
| Untreated fabric | — | — | — | — | — | ○ | 12.7 | 6.9 |
| Sample 6 (Comp. Example) | 0.55 | 0 | 0 | 0 | 0 | ○ | 12.6 | 6.9 |

*W: Washing

Example 2

Water was added to the mixture of 1 g of tetraisopalmitic acid ester as an ascorbic acid derivative (trade name: VC-IP, made by Nikko Chemicals Co., Ltd.), 5 g of squalane, 1 g of dodecanol, 0.8 g of anionic surfactant (trade name: Levenol WX, made by Kao Corp.) and 0.8 g of nonionic surfactant (trade name: Leodol, made by Kao Corp.) to 1 kg in total amount. The mixture was emulsified using a homogenizer to obtain an emulsion of the ascorbic acid derivative. Into this emulsion, 5 pieces each of cotton 100% fabric, cotton/polyester: 50/50 fabric, nylon 100% fabric, each 30 cm×30 cm in size, were dipped, squeezed at the squeezing rate of 90%, and subjected to the heat treatment at 120° C. for 5 minutes to obtain test fabrics of the samples 7 to 9. The test fabrics of the samples 7 to 9 were washed 10 times with the detergent for general washing (trade name: Attack, made by Kao Corp.) using a conventional washing machine, followed by measuring stuck amounts of the ascorbic acid derivative before and after the washing. Independently from these tests, evaluations of sustained discharge functions, moisture absorption and release properties, and feelings of the samples 7 to 9 were carried out. The evaluations of the sustained discharge functions were conducted by measuring remaining amounts of the ascorbic acid derivative after 1 time, 4 times and 10 times of washings. Results are shown in Table 3. In addition, on the untreated fabrics same to those used for the samples 7 to 9, respectively, evaluations of moisture absorption and release properties and feelings were carried out. Results are shown in Table 3.

In Table 3, all of the samples 7 to 9, which were the test fabrics treated with the emulsions containing the ascorbic acid derivative, showed remaining of 50% or more of the ascorbic acid derivative even after 10 times of washings, proving a very high resistance to washing. The sustained discharge function was similarly good. Furthermore, all of these samples showed better feelings in comparison with the untreated fabrics, respectively, and no reduction in the moisture absorption and release properties was observed by the treatment of the present invention.

TABLE 3

| Sample No. | Stuck amount (mg/g) Before W* | Stuck amount (mg/g) After 10 W* | Sustained discharge function (mg/g) After 1 W* | Sustained discharge function (mg/g) After 4 W* | Sustained discharge function (mg/g) After 10 W* | Feeling | Moisture absorption & release (%) Absorption | Moisture absorption & release (%) Release |
|---|---|---|---|---|---|---|---|---|
| Sample 7 (Cotton 100%) | 0.46 | 0.25 | 0.18 | 0.10 | 0.06 | ○ | 12.3 | 6.8 |
| Untreated fabric (Cotton 100%) | — | — | — | — | — | ○ | 12.7 | 6.9 |
| Sample 8 (Cotton/Polyester: 50/50) | 0.43 | 0.23 | 0.19 | 0.11 | 0.05 | ○ | 6.53 | 3.56 |
| Untreated fabric (Cotton/Polyester: 50/50) | — | — | — | — | — | ○ | 6.58 | 3.55 |
| Sample 9 (Nylon 100%) | 0.50 | 0.30 | 0.22 | 0.13 | 0.07 | ○ | 4.53 | 2.45 |
| Untreated fabric (Nylon 100%) | — | — | — | — | — | ○ | 4.55 | 2.47 |

*W: Washing

Example 3

A polynosic viscose solution (cellulose 5.0%, total alkali 3.5%, total sulpher 3.0%) was prepared according to the conventional method, then polypropyleneglycol diglycidylether (trade name: Denacol EX-931, made by Nagase Chemicals, Ltd.) added and homogeneously mixed so that the concentration became 5% by weight to cellulose in said viscose solution, and fine granular chitosan having 82% of a degree of deacetylation, 42,000 of an average molecular weight, 10 μm or less of a grain diameter were added and homogeneously mixed so that the concentrations became 1% by weight to the cellulose in said viscose solution, to obtain a spinning dope. The obtained dope was spun into a spinning bath containing 22 g/L of sulfuric acid, 65 g/L of sodium sulfate and 0.5 g/L of zinc sulfate at the temperature of 35° C. and the spinning speed of 30 m/min. using the nozzle of 0.07 mm Φ×500 H. Subsequently the yarn was drawn by 2 times in the bath containing 2 g/L of sulfuric acid and 0.05 g/L of zinc sulfate at 25° C., followed by cutting to the fiber length of 38 mm, then treating in the bath containing 1 g/L of sodium carbonate and 2 g/L of sodium sulfate at 60° C. and again in the bath containing 5 g/L of sulfuric acid at 65° C. In addition, the yarn was scoured, bleached and rinsed by the conventional methods, then subjected to the heat treatment at 130° C. for 15 minutes. The fiber was washed and dried again to produce 50 kg of the polynosic regenerated cellulose fiber containing the cross-linking agent and the fine granular chitosan and having 1.39 decitex. Subsequently, using the obtained said polynosic regenerated cellulose fiber, a spun yarn having the yarn count of 40 was produced from which a fabric was produced. Further, the obtained fabric was treated with the aqueous solution containing 5% by weight of ethyleneglycol diglycidylether (trade name: Denacol EX-810, made by Nagase Chemicals, Ltd.), then dried with a hot air at 130° C. for 15 minutes, followed by washing and drying to obtain a cross-linked fabric.

Similarly as in Example 1, tetraisopalmitic acid ester of ascorbic acid as an ascorbic acid derivative (trade name: VC-IP, made by Nikko Chemicals Co., Ltd. ), squalane, dodecanol, anionic surfactant (trade name: Levenol WX, made by Kao Corp.) and nonionic surfactant (trade name: Leodol, made by Kao Corp.) were mixed as shown in Table 4, respectively. Water was added to each mixture so that total amount of each mixture became 1 kg, followed by emulsifying using a homogenizer to obtain 5 kinds of emulsions of the ascorbic acid derivative, which were named as emulsions 8 to 12, respectively. Five pieces each of said cross-linked fabric having a size of 30 cm×30 cm were dipped into each of the emulsions 8 to 12, squeezed at the squeezing rate of 90%, subjected to the heat treatment at 120° C. for 5 minutes, to obtain the test fabrics of the samples 10 to 14. The obtained test fabrics of the samples 10 to 14 were washed 10 times with a detergent for general washing (trade name: Attack, made by Kao Corp.) using a conventional washing machine. Stuck amounts of ascorbic acid derivative of the samples 10 to 14 before and after the washing were measured. Independently from these tests, evaluations of sustained discharge functions and feelings of the samples 10 to 14 were carried out. The evaluations of the sustained discharge functions were conducted by measuring remaining amounts of the ascorbic acid derivative after 1 time, 4 times and 10 times of washings with additions of oleic acid to the samples 10 to 14, respectively. Results are shown in Table 5. In addition, evaluations of moisture absorption and release properties and feelings on the untreated fabric same to the one used for the samples 10 to 14 were also carried out. Results are also shown in Table 5.

In Table 5, the samples 11 to 14, which were the test fabrics treated with the emulsions containing 0.05 to 10% of the ascorbic acid derivative, showed remaining of 50% or more of the ascorbic acid derivative even after 10 times of washings, proving a very high resistance for washing. Further, in the sustained discharge function test in which washing was carried out with an addition of oleic acid, the sufficient level of sustained discharge function could be confirmed. Further, these test fabrics were also found to have swelling-suppressing property to water, fibrillation-preventing property and antibacterial function. However, the test fabric of the sample 1 which was treated with the emulsion containing 0.03% of the ascorbic acid derivative showed a low level of the initial stuck amount, and the remaining amount so remarkably decreased that remaining amount could hardly be found after one time of the washing with the addition of oleic acid, proving not to be able to give an sufficient level of the sustained discharge function. Furthermore, all of these samples did not show any decrease in the feeling and the moisture absorption and release properties in comparison with the untreated fabric.

TABLE 4

| Emulsion No. | VC-IP (g) | Squalane (g) | Dodecanol (g) | Nonionic surfactant (g) | Anionic surfactant (g) |
|---|---|---|---|---|---|
| Emulsion 8 | 0.3 | 1.5 | 0.3 | 0.2 | 0.2 |
| Emulsion 9 | 0.5 | 2.5 | 0.5 | 0.4 | 0.4 |
| Emulsion 10 | 1 | 5 | 1 | 0.8 | 0.8 |
| Emulsion 11 | 50 | — | 50 | 40 | 40 |
| Emulsion 12 | 100 | — | 100 | 80 | 80 |

TABLE 5

| Sample No. | Stuck amount (mg/g) | | Sustained discharge function (mg/g) | | | Feeling | Moisture absorption & release (%) | |
|---|---|---|---|---|---|---|---|---|
| | Before W* | After 10 W* | After 1 W* | After 4 W* | After 10 W* | | Absorption | Release |
| Sample 10 | 0.09 | 0 | 0 | 0 | 0 | ○ | 17.5 | 7.2 |
| Sample 11 | 0.31 | 0.16 | 0.20 | 0.09 | 0.01 | ○ | 17.4 | 7.3 |
| Sample 12 | 0.50 | 0.26 | 0.21 | 0.11 | 0.07 | ○ | 17.3 | 7.4 |
| Sample 13 | 20.3 | 10.3 | 9.1 | 7.8 | 1.7 | ○ | 17.3 | 7.4 |
| Sample 14 | 48.0 | 22.1 | 16.3 | 5.5 | 2.5 | ○ | 17.2 | 7.1 |
| Untreated fabric | — | — | — | — | — | ○ | 17.4 | 7.2 |

*W: Washing

Effect of the Invention

The present invention provides a functionalized fiber material wherein an ascorbic acid derivative which is hardly soluble in water is stuck on the fiber material and a method for treating therefor. By the treatment, a fiber material can be obtained which is excellent in the feeling for the clothing application and expected to have a skin care effect with a resistance to washing, that is, a skin care effect enabling a sustained discharge of an ascorbic acid derivative by an action of a fat component such as sebum present on a skin surface of the human body, without losing moisture absorption and release properties which are essentially possessed by the fiber itself.

What is claimed is:

1. A functionalized fiber material which comprises a tetraalkylester of L-ascorbic acid, which is substantially insoluble in water, adhered to a fiber material.

2. The functionalized fiber material according to claim 1, wherein the amount of the tetraalkylester of L-ascorbic acid adhered to the fiber material before washing is 0.30 to 48.0 mg/g.

3. A method for treating a fiber material which comprises treating said fiber material with an emulsion containing an ascorbic acid derivative which is substantially insoluble in water, said emulsion further including an anionic surfactant or a combination of an anionic surfactant and a nonionic surfactant.

4. The method for treating a fiber material according to claim 3, wherein the ascorbic acid derivative is tetraalkylester of L-ascorbic acid.

5. The method for treating a fiber material according to claim 3, wherein the ascorbic acid derivative is a tetraalkylester of L-ascorbic acid.

6. The method for treating a fiber material according to claim 3, wherein the concentration of the ascorbic acid derivative which is contained in the emulsion is 0.05 to 10% by weight.

7. The method for treating a fiber material according to claim 5, wherein a concentration of the tetraalkylester of L-ascorbic acid contained in the emulsion is 0.05 to 10% by weight.

8. The functionalized fiber material according to claim 1, wherein the amount of tetraalkylester of L-ascorbic acid adhered to the fiber material before washing is 0.30 to 48.0 mg/g.

9. A functionalized fiber material which comprises:
a emulsion containing a tetraalkylester of L-ascorbic acid which is substantially insoluble in water adhered to a fiber material.

10. The functionalized fiber material of claim 9, wherein the amount of tetraalkylester of L-ascorbic acid adhered to the fiber material before washing is 0.30 to 48.0 mg/g.

11. A textile material containing the functionalized fiber material of claim 1.

* * * * *